(12) United States Patent
Faulkner

(10) Patent No.: US 6,582,665 B2
(45) Date of Patent: Jun. 24, 2003

(54) UNIVERSAL COLLECTION AND TRANSFER SYSTEM

(75) Inventor: Michael T. Faulkner, Leominster, MA (US)

(73) Assignee: Biomedical Polymers, Inc., Gardner, MA (US)

(*) Notice: Subject to any disclaimer, the term of this patent is extended or adjusted under 35 U.S.C. 154(b) by 0 days.

(21) Appl. No.: 09/769,642

(22) Filed: Jan. 25, 2001

(65) Prior Publication Data

US 2002/0096469 A1 Jul. 25, 2002

(51) Int. Cl.⁷ .................... B01L 11/00; B01D 35/00
(52) U.S. Cl. .............. 422/101; 422/103; 210/233; 210/244; 210/407; 210/474; 210/498
(58) Field of Search ............... 210/173, 233, 210/244, 359, 383, 407, 446, 474, 498; 422/101, 103; 436/177

(56) References Cited

U.S. PATENT DOCUMENTS

| | | | | |
|---|---|---|---|---|
| 3,709,365 A | * | 1/1973 | Czaplinski et al. | 210/233 |
| 4,675,110 A | | 6/1987 | Fay | 210/436 |
| 4,800,020 A | * | 1/1989 | Savas et al. | 210/359 |
| 4,957,637 A | * | 9/1990 | Cornell | 210/359 |
| 5,364,533 A | * | 11/1994 | Ogura et al. | 210/504 |
| 5,624,554 A | | 4/1997 | Faulkner et al. | 210/232 |
| 6,296,763 B1 | * | 10/2001 | Hicks | 210/244 |

\* cited by examiner

*Primary Examiner*—Matthew O. Savage
(74) *Attorney, Agent, or Firm*—Iandiorio & Teska; Kirk Teska; R. Stephen Rosenholm

(57) ABSTRACT

A universal collection and transfer system which includes a collection container, a second container, and a transfer device mateable with both the collection container and the second container and including a hollow shaft which pierces the collection container to transfer a sample in the collection container into the second container.

40 Claims, 7 Drawing Sheets

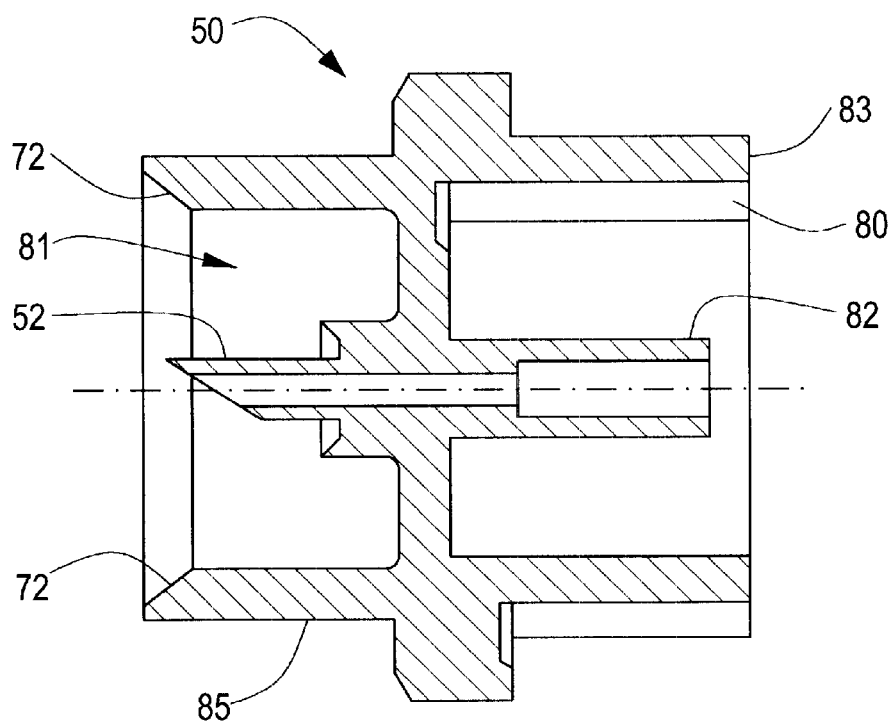
FIG. 11
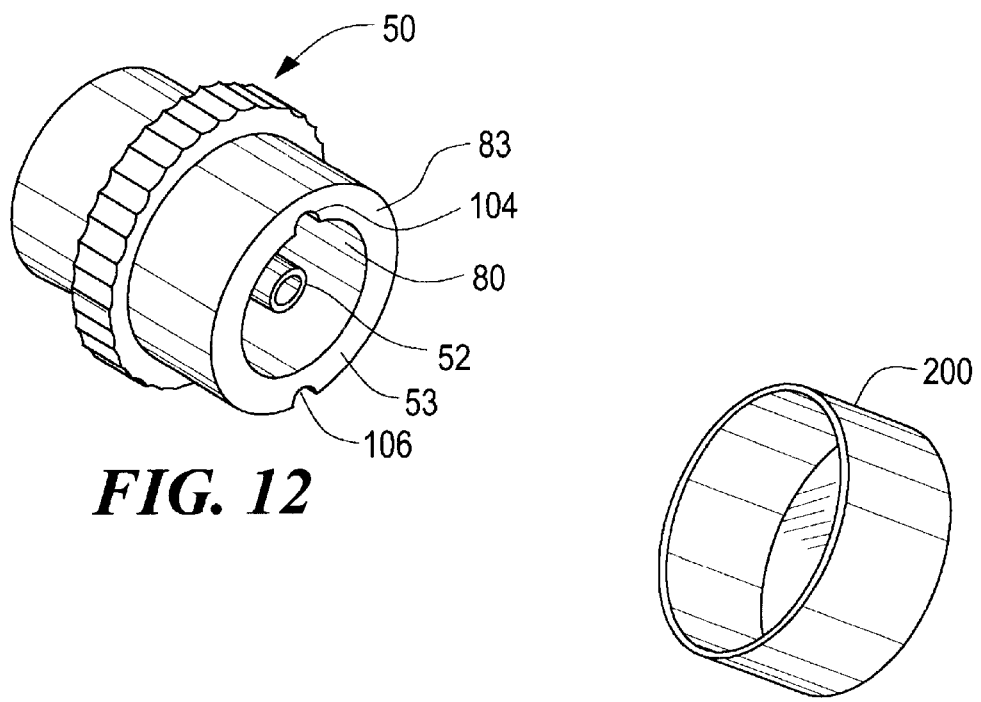
FIG. 12
FIG. 13

UNIVERSAL COLLECTION AND TRANSFER SYSTEM

FIELD OF THE INVENTION

This invention relates to an improved collection and transfer device for collecting, transferring, and filtering a medical sample.

BACKGROUND OF THE INVENTION

There are a number of applications, usually medical, in which solid particles are extracted from a liquid or slurry. The particles to be examined may be captured by a filter or may be passed by the filter while larger, undesired particles are blocked. One specific medical application includes the separation of parasite larva and eggs from a stool sample placed in a specimen vial or a collection container filled with a fixative or preservative. The devices used for this application are typically called "stool transportation and filtration systems." One improvement over previous devices is discussed in U.S. Pat. No. 4,675,110 assigned to the same entity as this application. In that device, one improvement involved the equalization of pressure between a collection vessel and an attached receptacle vessel. Another improvement is discussed in U.S. Pat. No. 5,624,554 also assigned to the same entity as this application. Both of these patents are hereby incorporated herein.

There are other devices on the market for collecting and filtering such samples but many do not offer a safe, closed system in which collection and transfer occurs without any chance of spillage. Some devices spill easily, others include filters susceptible to blockage, and still others require additional components in order to collect and agitate a sample or will only work properly with specially fabricated components. Many are difficult to use and may confuse laboratory technicians or worse, the patient.

In the simplest example, the patient places a stool sample in a collection container filled with a fixative, seals the collection container and then brings it or sends it to a laboratory. The laboratory technician then shakes the collection container to agitate the sample, slowly opens the collection container to prevent the sample from being forcefully ejected under pressure from the collection container, and then pours the sample into a funnel fitted with gauze to filter the sample before it is received in a centrifuge tube.

When this process is repeated multiple times in a given work day, it quickly becomes a complex, messy, and inconvenient process.

BRIEF SUMMARY OF THE INVENTION

It is therefore an object of this invention to provide a collection and transfer system which is more universal in design.

It is a further object of this invention to provide such a collection and transfer system which is simple to use.

It is a further object of this invention to provide such a collection and transfer system which eliminates the potential for spillage associated with many prior art collection and transfer systems.

It is a further object of this invention to provide such a collection and transfer system which overcomes the inconvenience associated with some prior art collection and transfer systems.

It is a further object of this invention of this invention to provide such a collection and transfer system which overcomes the problem of limited functionality associated with certain prior art collection and transfer systems.

The invention results from the realization that complexity, mess, inconvenience, and limited functionality associated with some prior art collection systems can be overcome by a transfer device which mates on one end with and includes a needle for piercing the bottom of a collection container and which mates on the other end with different size centrifuge tubes to transfer a specimen from the bottom of the collection container or any collection vials through the needle and into the centrifuge tube. This invention results from the further realization that the specimen can be pre-filtered and agitated while it is still in the collection container by including a filter element with agitating vanes in the collection container itself.

This invention features a universal collection and transfer system. The primary components typically include a collection container with an open upper end, a filter which divides the container into upper and lower sections, an agitator, and a closed bottom with a piercable portion. Also included is a transfer device including a slender hollow shaft for piercing the piercable portion of the bottom of the collection container in order to hygienically transfer a filtered sample from the collection container to a second container. The agitator may include a plurality of vanes upstanding from the filter. Preferably, the collection container includes a wall extending from the bottom thereof defining a chamber for receiving the transfer device therein. The closed bottom of the collection container is typically funnel shaped and terminates in the piercable portion. The filter may be disposed over the top of the funnel shaped bottom. Then, the transfer device includes a concave wall surrounding the shaft which mates with the funnel shaped bottom of the collection container to align the shaft with the pierceable portion of the bottom of the collection container.

The transfer device may further include further an opening in the bottom thereof defining a chamber of receiving the second container. A tube may be located in the opening in fluid communication with the hollow shaft. One or more vents may be provided in the transfer device for relieving pressure in the second container.

The collection container is typically made of a plastic material and has side walls which can be deflected inward to force the filtered sample out of the collection container, through the transfer device, and into the second container. The transfer device is also typically made of a plastic material. In many embodiments, the second container is a centrifuge tube.

A universal collection and transfer system according to this invention includes a collection container, a second container, and a transfer device mateable with both the collection container and the second container and including a hollow shaft which pierces the collection container to transfer a sample in the collection container into the second container. A collection container in accordance with this invention has an open upper end, a filter which divides the container into upper and lower sections, an agitator, and a closed bottom with a pierceable portion.

BRIEF DESCRIPTION OF THE DRAWINGS

Other objects, features and advantages will occur to those skilled in the art from the following description of a preferred embodiment and the accompanying drawings, in which:

FIG. 11 is a cross sectional view of the transfer device of the subject invention;

FIG. 12 is a schematic view of the transfer device shown in FIG. 11; and

FIG. 13 is a schematic view of the cap or plug which can be used in conjunction with the transfer device shown in FIGS. 11-12.

DISCLOSURE OF THE PREFERRED EMBODIMENTS

Figure 2:
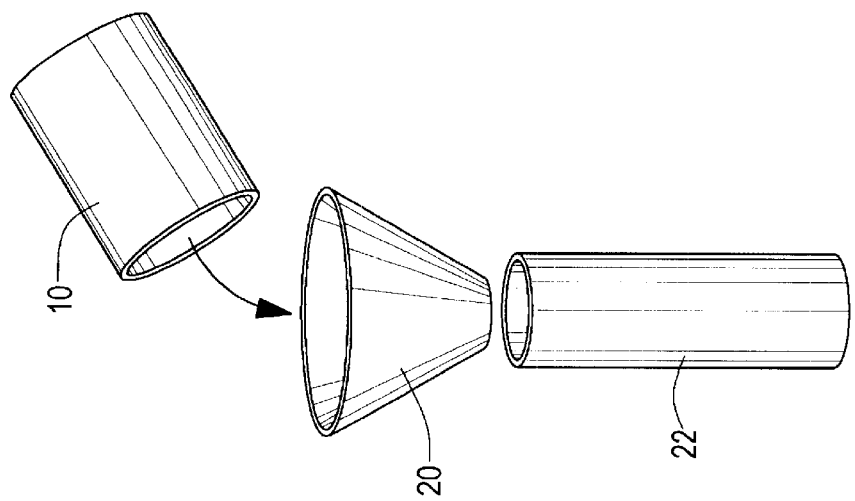
FIG. 2 is a schematic view showing the primary components associated with transferring and filtering a sample from a collection container to a centrifuge tube in accordance with the prior art collection container shown in FIG. 1.
Figure 1:
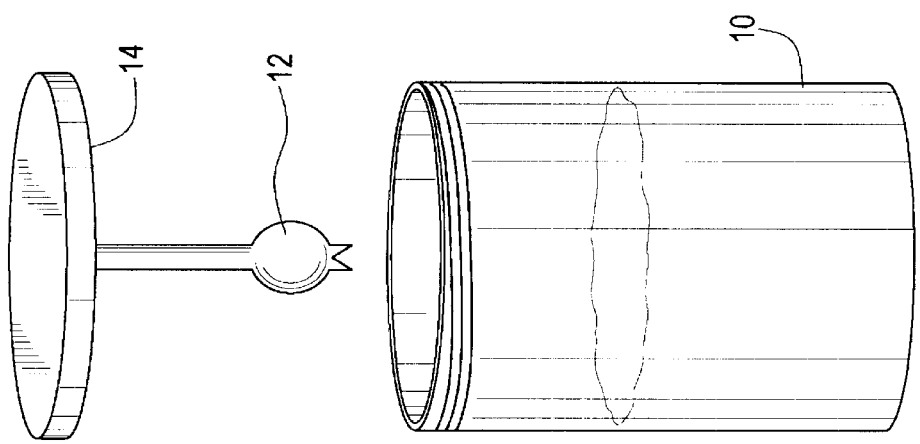
FIG. 1 is a schematic view of one prior art specimen collection container.

As delineated above in the Background section, it is fairly common for a patient to place a stool sample in prior art collection container 10, FIG. 1 filled with a predetermined about of fixative using spoon 12 which is an integral part of cap 14. The patient then seals collection container 12 with cap 14 and brings it to a laboratory for testing. Subsequently, the laboratory technician shakes collection container 10 to agitate the sample and then slowly opens cap 14 to prevent the sample from being forcefully ejected from the collection container under the pressure which builds up inside collection container 10. As shown in FIG. 2, the laboratory technician then pours the contents of collection container 10 into the wide end of funnel 20. Funnel 20 may be fitted with gauze (not shown) to filter the sample before it is received in centrifuge tube 22. Since this process is often repeated multiple times in a given work day, it has the potential to quickly become a fairly complex, time consuming, messy, and inconvenient process.

The universal collection and transfer system 30, FIGS. 3–12 of the subject invention addresses many if not all of these problems. Collection container 32 includes open upper end 34, filter element 36 (see FIG. 10) which divides container 32 into upper 38 and lower 40 sections, and an agitator subsystem which is typically integral with filter element 36 in the form of vanes 42 upstanding from filter element 36 as shown. Collection container 32 also includes closed bottom 44 with a pierceable portion 46.

Transfer device 50 is also a component of universal collection and transfer system 30. Transfer device 50 includes a slender hollow shaft 52 (for example a plastic needle) for piercing the pierceable portion 46 of the bottom 44 of collection container 32 in order to hygienically transfer a filtered sample from collection container 32 to a second container such as centrifuge vial 60.

Transfer device 50 is configured to mate on one end (end 51) with the bottom of collection container 32 and also to mate on the opposite end 53 with the open top 55 of centrifuge vial 60.

Figure 4:
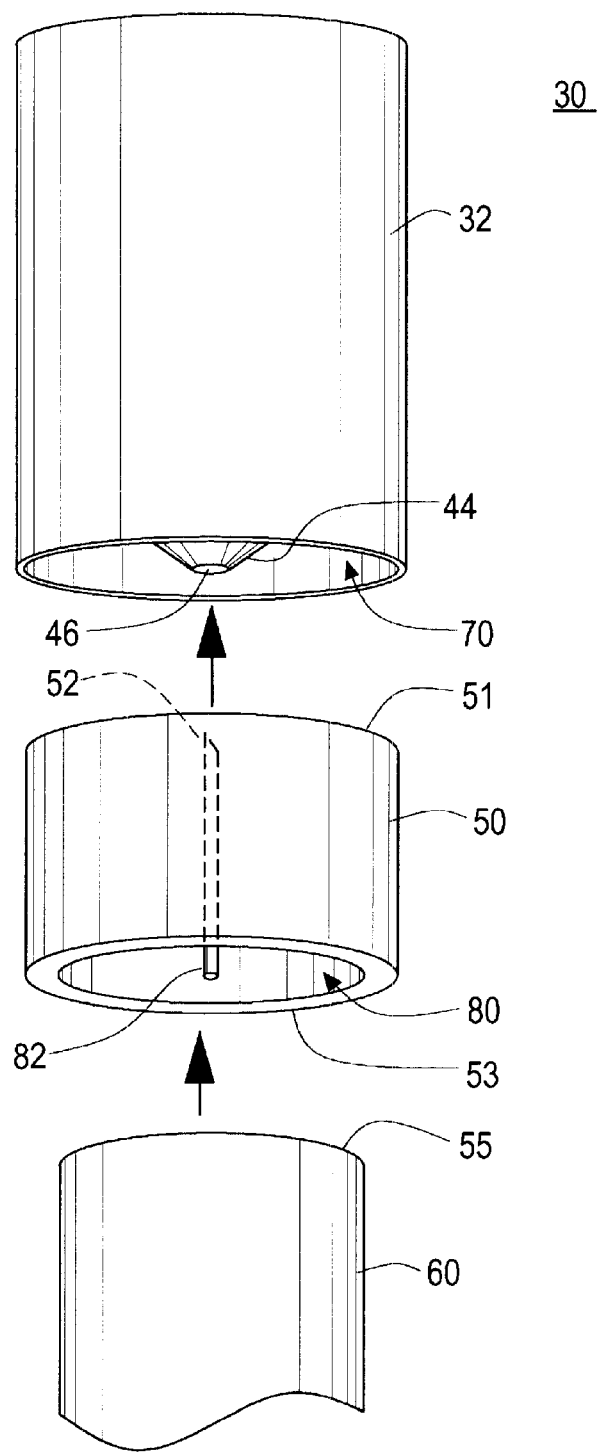
FIG. 4 is another exploded schematic view of the primary components associated with the universal collection and transfer system of the subject invention.

Accordingly, collection container 32 preferably includes wall 70, FIG. 4 extending downward around bottom portion 44 defining a chamber for receiving transfer device 50 therein such that needle 52 properly pierces pierceable portion 46 of the bottom 44 of collection container 32. To properly mate the bottom of collection container 32 with transfer device 50, the bottom 44 of collection container 32 is preferably funnel shaped as shown terminating in pierceable portion 46.

Figure 3:
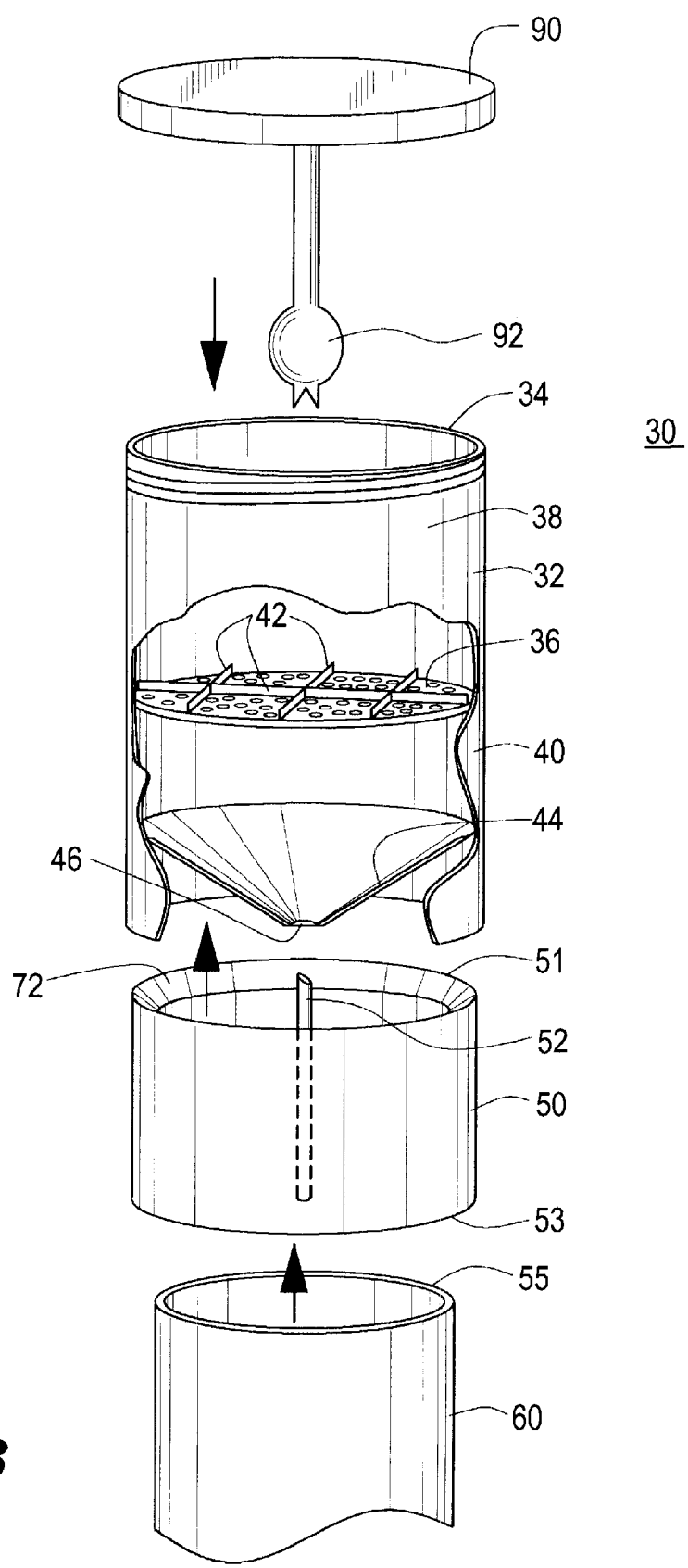
FIG. 3 is an exploded schematic view showing the primary components associated with the universal collection and transfer system of the subject invention.

Transfer device 50, as shown in FIG. 3, includes concave wall 72 surrounding shaft 52 which mates with the funnel shaped bottom 44, FIG. 4 of collection container 32 to correctly align shaft 52 of transfer device 50 with the piercable portion 46 of the bottom 44 of collection container 32. Filter element 36, FIG. 3 is disposed over the top of funnel shaped bottom 44 as shown in FIG. 3 thus eliminating the need for a separate funnel with gauze as discussed with respect to the prior art specimen collector shown in FIG. 2. Transfer device 50, FIG. 4 in turn, includes opening 80 in the bottom thereof as shown defining a chamber which receives the open top 55 of centrifuge vial 60. Tube 82 is typically centrally disposed within opening 80 and in fluid communication with hollow shaft 52 in order to transfer the medical sample from the bottom 44 of collection container 32 and into centrifuge vial 60.

Figure 5:
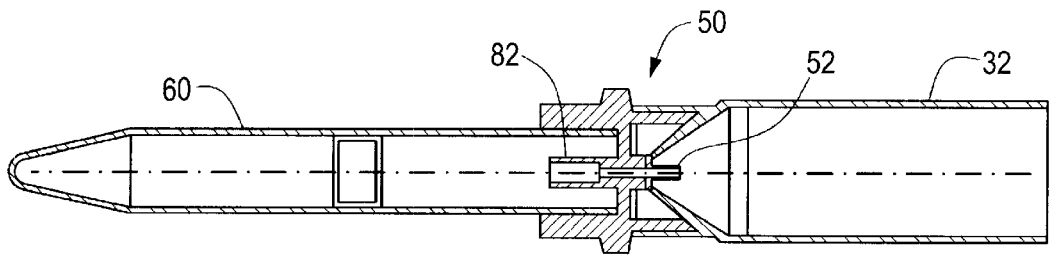
FIG. 5 is a cross sectional view of the three primary components of the universal collection and transfer system of the subject invention assembled for transferring a sample from the collection container to a centrifuge tube.

As shown in FIGS. 5–9, transfer device 50 couples collection container 32 to a second container such as centrifuge tube 60. Thus, system 30, FIGS. 3–5 is as used as follows. First, the patient removes cap 90, FIG. 3 (which typically includes integral collection spoon 92), from collection container 32. The patient then places a stool sample using spoon 90 inside collection container 32 which is partially filled with a fixative and seals the same using cap 90. While collection container 32 is in transit to the laboratory, agitating vanes 42 provide a homogenous mixture of the substances within collection container 32 and filter element 36 in the form of a thin plastic plate with a number of holes therethrough allows only certain size particles to filter down into the bottom portion 40 of collection container 32. The laboratory technician then uses transfer device 50 coupled on its bottom end 53 to centrifuge tube 60 as follows. Leaving cap 90 in place, the technician first drives transfer device 50 into the bottom 44 of collection container 32 whereupon shaft 52 pierces pierceable portion 46 of the bottom 44 of container 32. The laboratory technician then squeezes pliable collection container 32 to force the correct amount of the filtered sample (for example 3 ml.) out of the bottom 40 of collection container 32, through transfer device 50, and into centrifuge tube 60.

Figure 6:
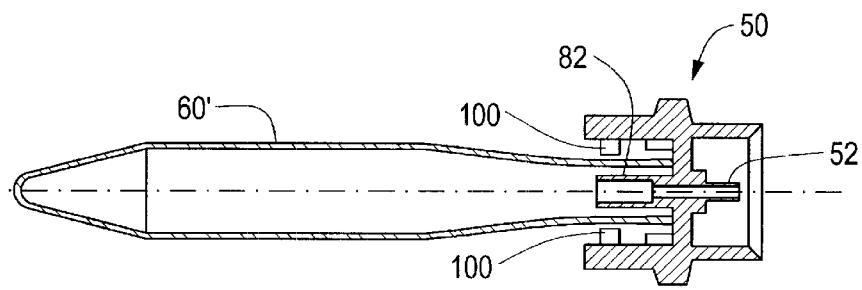
FIG. 6 is similar to FIG. 5 except the centrifuge tube is smaller.
Figure 7:
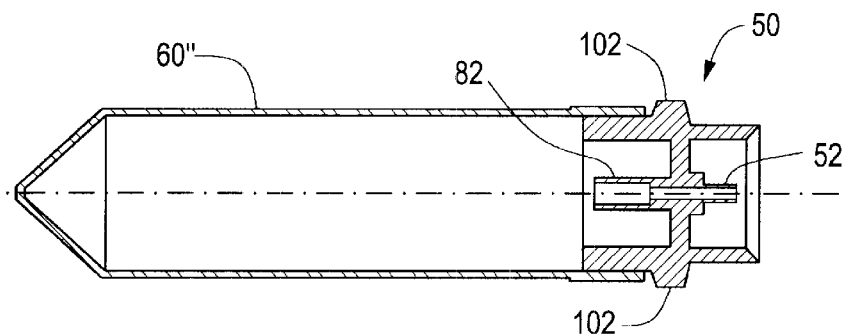
FIG. 7 is also similar to FIG. 5 except the centrifuge tube is larger.

As shown in FIGS. 5–7, transfer device 50 in one embodiment includes means for mating it with vials of different sizes, e.g., "spincan" vial 60 FIG. 5, 15 ml or smaller vial 60'; FIG. 6, and 50 ml or larger vial 60" FIG. 7. Ledge 100 FIG. 6 on the inside of opening 72 (FIG. 9) reduces the size of opening 72 for 15 ml or smaller vials while ledge 102 accepts 50 ml or larger vials. Air vents 104 and 106 FIG. 12 relieve any pressure in the second container.

Figure 10:
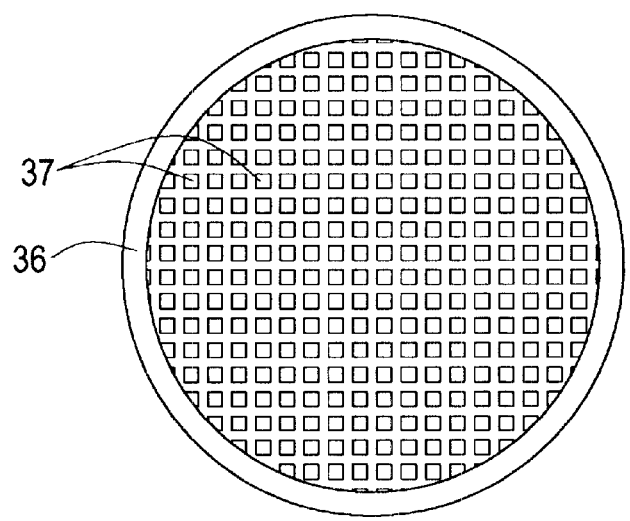
FIG. 10 is a top view of the filter element of the subject invention.

In the preferred embodiment, filter element 36, FIG. 10 includes orifices 37 0.030" square. Filter element 36 is 1.033" in diameter and 0.125" thick. Transfer device 50, FIG. 11 is 1.240" long. Concave wall 72 defines an opening which spans 82°. The distal end of needle 52 is cut at an angle of 31°. Opening 80 is about 0.8" in diameter while opening 81 is 0.733" in diameter. Walls 83 and 85 are about 0.177" thick.

Cap or plug 200, FIG. 13 may be included as a part of the kit to seal opening 80, FIG. 12 of transfer device 50 once a sample has been transferred therethrough and into the centrifuge vial in order to store the original sample in case further testing or analysis is required.

Figure 8:
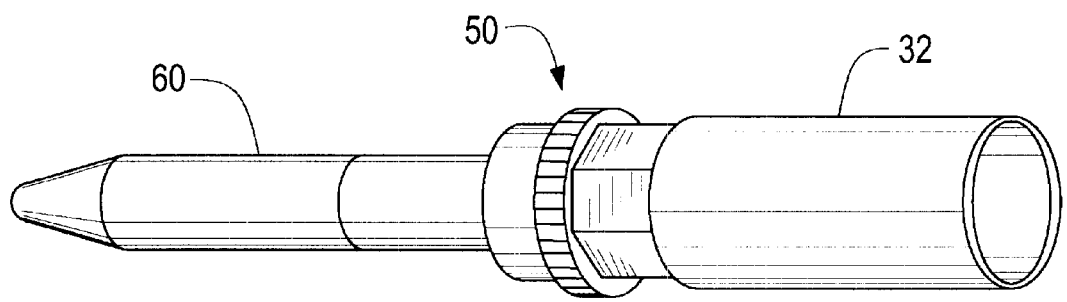
FIG. 8 is a schematic view showing the three primary components of the system of this invention.
Figure 9:
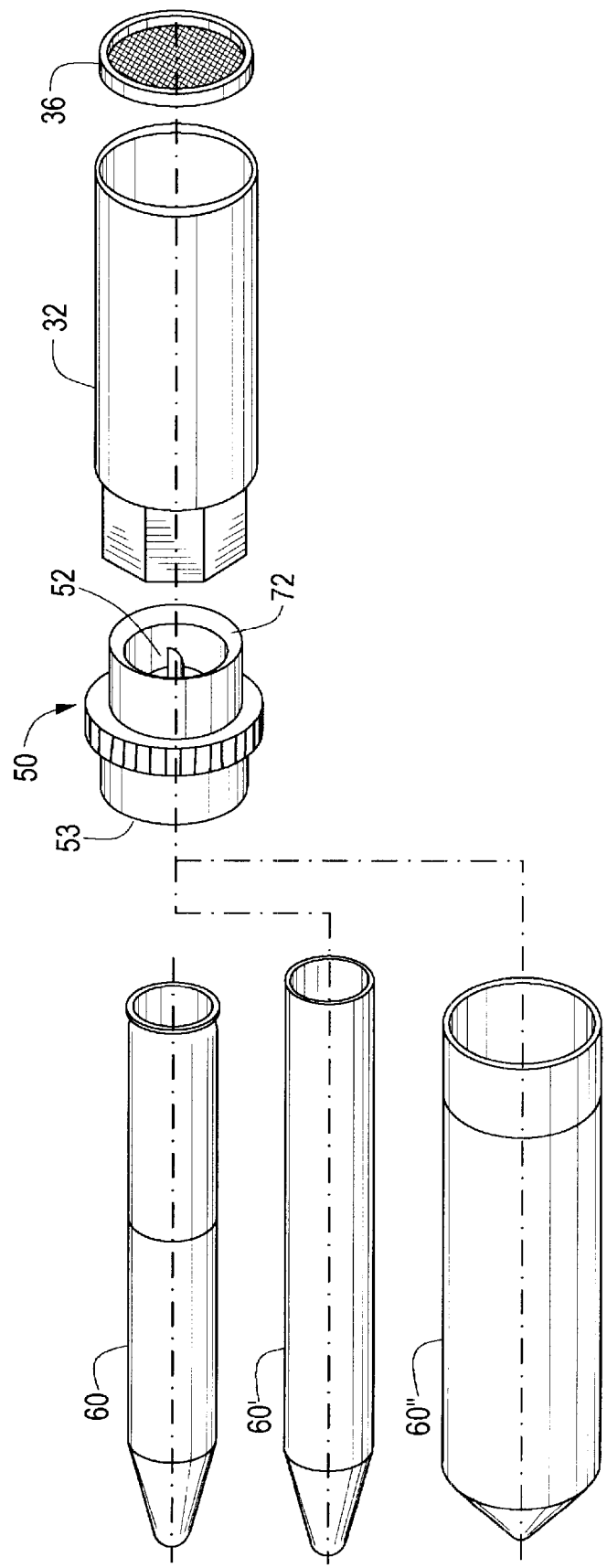
FIG. 9 is an exploded view of the system of this invention showing how the transfer device can be used in conjunction with different size and different style centrifuge vials.

Typically, all of the components are made of molded plastic especially collection container 32 FIGS. 8–9 which includes a side wall which can be deflected inactive to force a filtered sample out of the collection container, through the transfer device, and into the centrifuge vial.

Thus, the complexity, mess, inconvenience, and limited functionality associated with some prior art collection systems is overcome by transfer device 50, FIG. 3 which mates on one end with and includes needle 52 for piercing the bottom 44 of collection container 32 and which mates on the other end with different size centrifuge tubes 60 to transfer a specimen from the bottom 44 of collection container 32 through needle 52 and into centrifuge tube 60. The specimen is pre-filtered and agitated while it is still in collection container 32 by the addition of filter element 36 with agitating vanes 42 fitted within collection container 32.

Although specific features of the invention are shown in some drawings and not in others, this is for convenience only as each feature may be combined with any or all of the other features in accordance with the invention. The words "including", "comprising", "having", and "with" as used herein are to be interpreted broadly and comprehensively and are not limited to any physical interconnection. Moreover, any embodiments disclosed in the subject application are not to be taken as the only possible embodiments. Moreover, other embodiments will occur to those skilled in the art and are within the following claims:

What is claimed is:

1. A universal collection and transfer system comprising:
   a collection container including:
      an open upper end,
      a filter which divides the container into upper and lower sections,
      an agitator, and
      a closed bottom with a piercable portion;
   a transfer device including:
      a slender hollow shaft for piercing the piercable portion of the bottom of the collection container in order to hygienically transfer a filtered sample from the collection container to a second container; and
   where the collection container includes a wall extending from the bottom thereof defining a chamber for receiving the transfer device therein.

2. The system of claim 1 in which the agitator includes a plurality of vanes upstanding from the filter.

3. The system of claim 1 in which the closed bottom is funnel shaped and terminates in the piercable portion.

4. The system of claim 3 in which the filter is disposed over the top of the funnel shaped bottom.

5. The system of claim 3 in which the transfer device includes a concave wall surrounding the shaft which mates with the funnel shaped bottom of the collection container to align the shaft with the pierceable portion of the bottom of the collection container.

6. The system of claim 1 in which the transfer device includes an opening in the bottom thereof defining a chamber for receiving the second container and in which the transfer device further includes a tube located in the opening in fluid communication with the hollow shaft.

7. The system of claim 6 in which the transfer device further includes means for mating the transfer device with second containers of different sizes.

8. The system of claim 7 in which said means includes a ledge in the opening.

9. The system of claim 7 in which said means includes a ledge on the outside of the transfer device.

10. The system of claim 6 further including a cap for sealing the opening in the transfer device.

11. The system of claim 6 in which the chamber includes at least one vent for relieving pressure in the second container.

12. The system of claim 1 in which the collection container is made of a plastic material and has side walls which can be deflected inward to force the filtered sample out of the collection container, through the transfer device, and into the second container.

13. The system of claim 1 in which the transfer device is made of a plastic material.

14. The system of claim 1 including a second container that is a centrifuge tube.

15. The system of claim 14 in which the centrifuge tube is made of plastic.

16. A universal collection and transfer system comprising:
   a collection container including:
      an open upper end,
      a filter which divides the container into upper and lower sections,
      an agitator, and
      a closed bottom with a piercable portion wherein the closed bottom is funnel shaped and terminates in the piercable portion;
   a second container; and
   a transfer device mateable with both the collection container and the second container and including a hollow shaft which pierces the collection container to transfer a sample in the collection container into the second container.

17. The system of claim 16 in which the agitator includes a plurality of vanes upstanding from the filter.

18. The system of claim 16 in which the collection container further includes a wall extending from the bottom thereof defining a chamber for receiving the transfer device therein.

19. The system of claim 16 in which the filter is disposed over the top of the funnel shaped bottom.

20. The system of claim 16 which the transfer device includes a concave wall surrounding the shaft which mates with the funnel shaped bottom of the collection container to align the shaft with the pierceable portion of the bottom of the collection container.

21. The system of claim 16 in which the transfer device includes an opening in the bottom thereof defining a chamber for receiving the second container and in which the transfer device further includes a tube located in the opening in fluid communication with the hollow shaft.

22. The system of claim 21 in which the transfer device further includes means for mating the transfer device with second containers of different sizes.

23. The system of claim 22 in which said means includes a ledge in the opening.

24. The system of claim 22 in which said means includes a ledge on the outside of the transfer device.

25. The system of claim 21 further including a cap for sealing the opening in the transfer device.

26. The system of claim 21 in which the chamber includes at least one vent for relieving pressure in the second container.

27. The system of claim 16 in which the collection container is made of a plastic material and has side walls which can be deflected inward to force the filtered sample out of the collection container, through the transfer device, and into the second container.

28. The system of claim 16 in which the transfer device is made of a plastic material.

29. The system of claim 16 in which the second container is a centrifuge tube.

30. A collection container comprising:
    an open upper end;
    a filter which divides the container into upper and lower sections;
    an agitator;
    a closed bottom with a pierceable portion; and
    a wall extending from the bottom thereof defining a chamber for receiving a transfer device therein.

31. The system of claim 30 in which the agitator includes a plurality of vanes upstanding from the filter.

32. The system of claim 30 in which the closed bottom is funnel shaped and terminates in the piercable portion.

33. A transfer device comprising:
    a slender hollow shaft for piercing a bottom of a collection container in order to hygienically transfer a filtered sample from the collection container into a second container;
    an opening defining a chamber for receiving the second container;
    means for mating the transfer device with second containers of different sizes, a ledge on the outside of the transfer device.

34. The device of claim 33 in which the transfer device includes a concave wall surrounding the shaft.

35. The device of claim 33 in which said means includes a ledge in the opening.

36. The device of claim 33 further including a cap for sealing the opening of the transfer device.

37. The device of claim 33 in which the chamber includes at least one vent for relieving pressure in the second container.

38. A transfer device comprising:
    a slender hollow shaft for piercing a bottom of a collection container in order to hygienically transfer a filtered sample from the collection container into a second container;
    an opening defining a chamber for receiving the second container;
    means for mating the transfer device with second containers of different sizes, including a ledge in the opening.

39. The device of claim 38 in which the transfer device includes a concave wall surrounding the shaft.

40. The device of claim 38 in which said means includes a ledge on the outside of the transfer device.

* * * * *